US009981099B2

United States Patent
Feldhahn et al.

(10) Patent No.: US 9,981,099 B2
(45) Date of Patent: May 29, 2018

(54) DEVICE FOR ARTIFICIAL RESPIRATION

(71) Applicant: WEINMANN GERAETE FUER MEDIZIN GMBH & CO. KG, Hamburg (DE)

(72) Inventors: Karl-Andreas Feldhahn, Hamburg (DE); Heiko Sepke, Lütjensee (DE); Karl-Heinz Koenig, Norderstedt (DE); Christof Goebel, Hamburg (DE); Christian Kluin, Hamburg (DE); Joachim Gardein, Icod de los Vinos (ES)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 502 days.

(21) Appl. No.: 14/670,877

(22) Filed: Mar. 27, 2015

(65) Prior Publication Data
US 2015/0273167 A1  Oct. 1, 2015

(30) Foreign Application Priority Data

Mar. 28, 2014  (DE) .................. 10 2014 004 850

(51) Int. Cl.
*A61M 16/10*  (2006.01)
*A61M 16/00*  (2006.01)
(Continued)

(52) U.S. Cl.
CPC .... *A61M 16/0069* (2014.02); *A61M 16/0066* (2013.01); *A61M 16/021* (2017.08); *A61M 16/04* (2013.01); *A61M 16/06* (2013.01); *A61M 16/16* (2013.01); *A61M 16/109* (2014.02); *A61M 2016/0027* (2013.01); *A61M 2016/0033* (2013.01); *A61M 2205/33* (2013.01);
(Continued)

(58) Field of Classification Search
CPC .......... A61M 16/0066; A61M 16/0069; A61M 16/16; A61M 2016/0027; A61M 2016/03; A61M 2016/033; A61M 2205/3553; A61M 2205/3569; A61M 2205/3584; A61M 2205/3592; A61M 2205/42; A61M 2205/502; A61M 2205/505
See application file for complete search history.

(56) References Cited

U.S. PATENT DOCUMENTS

| 7,975,688 B1 | 7/2011 | Truit |
| 2007/0193580 A1* | 8/2007 | Feldhahn ............... A61M 16/00 128/204.18 |

(Continued)

FOREIGN PATENT DOCUMENTS

| EP | 2703034 A2 | 3/2014 |
| WO | 9922793 A1 | 5/1999 |

(Continued)

*Primary Examiner* — Lynne Anderson
(74) *Attorney, Agent, or Firm* — Abel Law Group, LLP

(57) ABSTRACT

The disclosed device serves for artificial respiration and has a blower connected to a control. The blower is held by a supporting part, which assumes the task of decoupling and other functions. The blower and the supporting part are arranged in a blower box. Both the control and the blower box are arranged in a housing. The control is connected to at least one indicating device and also to at least one operating element.

20 Claims, 14 Drawing Sheets

(51) Int. Cl.
 *A61M 16/16* (2006.01)
 *A61M 16/04* (2006.01)
 *A61M 16/06* (2006.01)

(52) U.S. Cl.
 CPC ............... *A61M 2205/3553* (2013.01); *A61M 2205/3569* (2013.01); *A61M 2205/3584* (2013.01); *A61M 2205/3592* (2013.01); *A61M 2205/42* (2013.01); *A61M 2205/502* (2013.01); *A61M 2205/505* (2013.01); *A61M 2205/52* (2013.01); *A61M 2230/04* (2013.01); *A61M 2230/10* (2013.01); *A61M 2230/14* (2013.01); *A61M 2230/205* (2013.01); *A61M 2230/50* (2013.01); *A61M 2230/60* (2013.01); *A61M 2230/62* (2013.01)

(56) References Cited

U.S. PATENT DOCUMENTS

| | | |
|---|---|---|
| 2010/0307498 A1 | 12/2010 | Jones et al. |
| 2014/0158131 A1 | 6/2014 | Kenyon et al. |
| 2015/0023782 A1 | 1/2015 | Velzy et al. |

FOREIGN PATENT DOCUMENTS

| | | |
|---|---|---|
| WO | 2013020167 A1 | 2/2013 |
| WO | 2013133889 A1 | 9/2013 |

* cited by examiner

DEVICE FOR ARTIFICIAL RESPIRATION

CROSS-REFERENCE TO RELATED APPLICATIONS

The present application claims priority under 35 U.S.C. § 119 of German Patent Application No. 10 2014 004 850.0, filed Mar. 28, 2014, the entire disclosure of which is expressly incorporated by reference herein.

BACKGROUND OF THE INVENTION

1. Field of the Invention

The invention relates to a device for artificial respiration, which has a blower connected to a control, wherein both the control and the blower are arranged in a housing, and wherein the control is connected to at least one indicating device and also at least one operating element.

2. Discussion of Background Information

Such devices for artificial respiration are typically connected to a supply system for being supplied with power and connected to a respiration mask by means of a respiratory tube. A patient puts on the respiration mask in the area of the face while the artificial respiration is being carried out.

For example, it is known to use such devices for artificial respiration for carrying out CPAP therapy, APAP therapy or bilevel ventilation. In principle, any desired respiration sequences can be preset by the control of the device.

It would be advantageous to design of a device of the type mentioned at the beginning in such a way that improved quality of use is provided.

SUMMARY OF THE INVENTION

The device for artificial respiration according to the invention has a blower connected to a control, wherein both the control and the blower are arranged in a housing, and wherein the control is connected to at least one indicating device and also at least one operating element and wherein the blower is secured in the housing by a viscoelastic or elastomeric supporting part.

In one aspect of the device, the housing may comprise a front unit, which has the indicating device, and two further housing parts, which form a blower box.

In another aspect of the device of the invention, the supporting part may be secured between the housing parts, the two housing parts respectively having the associated chamber halves of the high-pressure region and the intake region.

In yet another aspect of the device, the supporting part may be arranged in the vertical direction between the housing parts.

In a still further aspect of the device, the supporting part may form a first seal, which provides a seal with respect to sealing surfaces of the housing parts, and may form a second seal, which provides a seal with respect to sealing surfaces of the two housing parts and pneumatically separates the high-pressure region from the intake region.

In another aspect of the device, the supporting part in the blower box may serve for redirecting the air, and consequently reducing the noise, and for this purpose may have at least two openings.

In another aspect of the device, the supporting part may have at least one opening that is surrounded at least in certain portions by a collar.

In another aspect of the device, the supporting part may serve for directing the air flows and has for this purpose openings or apertures, and/or the supporting part likewise may serve for sound damping and for this purpose has a collar at least on one of the openings, and/or the supporting part likewise may serve for sound decoupling and securing the blower and is therefore produced from an elastomeric material and for this purpose has a coupling element for securing the blower, wherein the coupling element may also have beads, and the supporting part also may have at least one seal for providing a seal of the housing parts with respect to the surroundings and a further seal for providing a seal of the intake region and the high-pressure region, and/or the supporting part may also be held between the housing parts by clamping or bracing or screwing.

In another aspect of the device of the invention, at least three redirecting features may be arranged within the blower box for a flow of respiratory gas.

In another aspect of the device of the invention, at least one sound-damping element may be arranged within the blower box and/or on the supporting part.

In another aspect of the device of the invention, the indicating device and also a front sheet that has at least one operating element may be accommodated in the front unit.

In another aspect of the device of the invention, an indicating device may be arranged in an inclined manner in relation to the vertical direction.

In another aspect of the device of the invention, the housing may have a triangular cross-sectional area.

In another aspect of the device of the invention, the front unit may comprise or consists of a vertically extending first segment and a second segment, which is inclined in relation to the vertical direction and in which an indicating device is arranged.

In another aspect of the device of the invention, the indicating device may be formed as a panel-like display, which is fixed in the front unit by a frame-like securing element.

In another aspect of the device of the invention, the securing element may provide a clasp for fixing the display or the securing element may be capable of being screwed in the front unit.

In another aspect of the device of the invention, just one mechanical operating element may be provided for the activation of a device function.

In another aspect of the device of the invention, in addition to the just one mechanical operating element, further operating areas may be provided on the display formed as a touchscreen.

In another aspect of the device of the invention, a line routing for the connection of a pressure measurement comprising a line portion of a first diameter and a line portion of a second diameter may be formed within the device, the second diameter being less than the first diameter.

BRIEF DESCRIPTION OF THE DRAWINGS

Exemplary embodiments of the invention are schematically represented in the drawings, in which.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
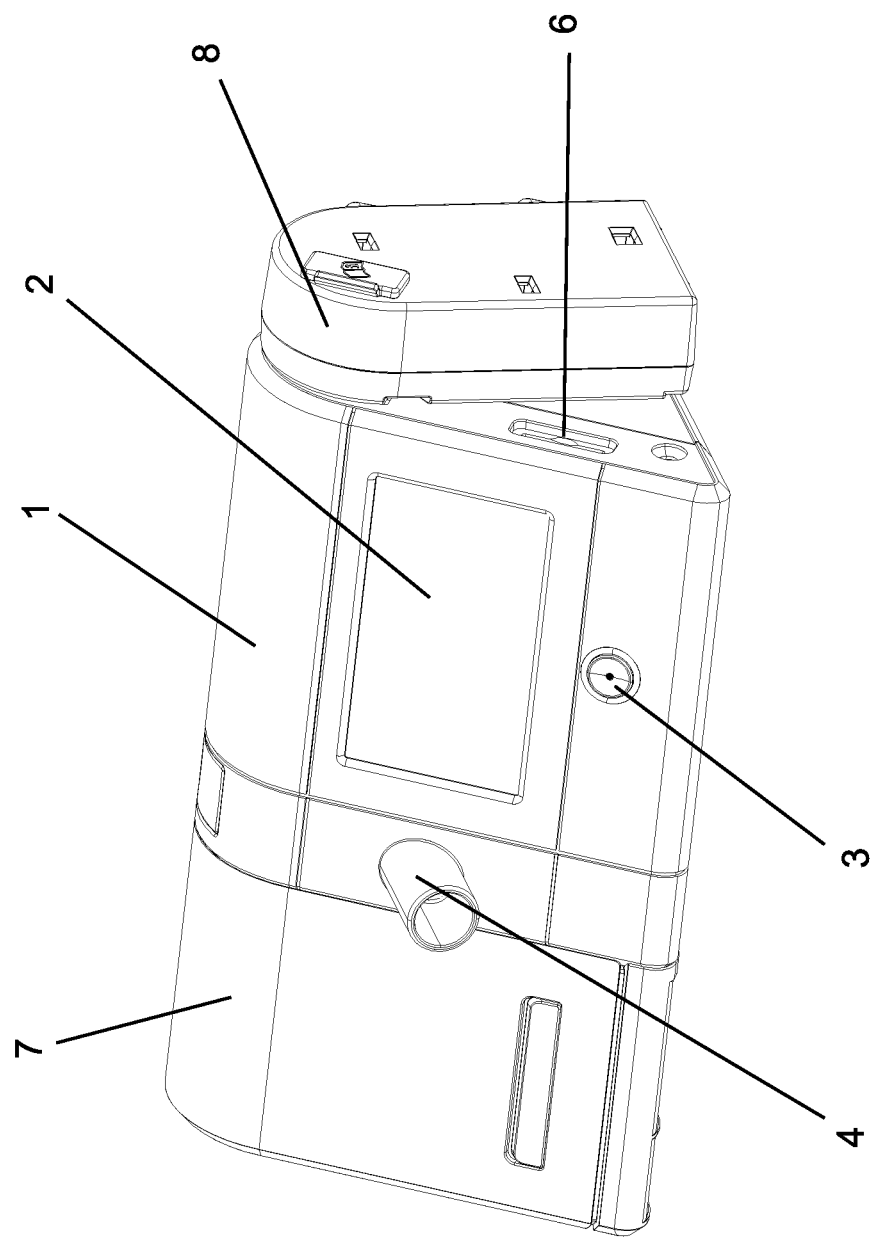
FIG. 1 shows a perspective representation of a device with an obliquely arranged display.

FIG. 1 shows a respirator (1). The respirator (1) is provided with an indicating device (2), at least one operating element (3) and also a tube connection (4).

The tube connection (4) typically serves for connection to a respiratory gas tube (not represented), which is connected in the region of its extent that is away from the tube connection (4) to a breathing mask that is likewise not represented. The breathing mask that is not represented serves for supplying respiratory gas to a patient, who is likewise not represented. An electrical connection (not represented) for heating a respiratory tube may be optionally provided in the region of the tube connection.

The respirator (1) is typically provided with at least one communication interface (6). Here, the interface (6) is arranged in a side region. The interface (6) is inclined in relation to the horizontal and is in the spatial vicinity of the display. The respirator preferably also has an interface (6') that serves for the coupling of modules (8).

In the case of the exemplary embodiment represented, the respirator (1) is coupled with a respiratory gas humidifier (7). The respirator (1) may be operated optionally both with and without the respiratory gas humidifier (7).

According to the embodiment represented in FIG. 1, the housing of the respirator (1) has a triangular cross-sectional area in a vertical sectional plane.

According to the embodiment in FIG. 1, additional elements (8), which provide at least one further device function, can be coupled to the respirator (1) as and when required. The display (13) is formed here as a user interface, for example as a touchscreen, of the respirator (1). In the region of the display (13), a number of input buttons configured for receiving a user input are provided. The display (13) is connected by logic circuitry to the buttons and has a number of information fields, wherein each information field is assigned to a corresponding input button and configured for indicating graphic items of information that specify various functions of the corresponding input buttons. The input buttons are touch-sensitive areas in the region of the display (13). According to the invention, at least one further operating element (3) is provided. This operating element (3) can be operated mechanically, and consequently differs from the touch areas on the display. According to the invention, the respirator is switched on and off by means of the operating element (3), so that a basic patient-specific therapy can be activated by means of just one button. For this purpose, the operating element (3) is connected by logic circuitry to the blower motor and activates it, and also the memory, in order to retrieve and apply stored therapy data, such as pressure values. In addition, adaptation of individual values, such as pressure values, may take place by means of the input buttons. However, according to the invention, it is not necessary to use the input buttons to operate the touchscreen (13) in order to start the therapy.

Figure 2:
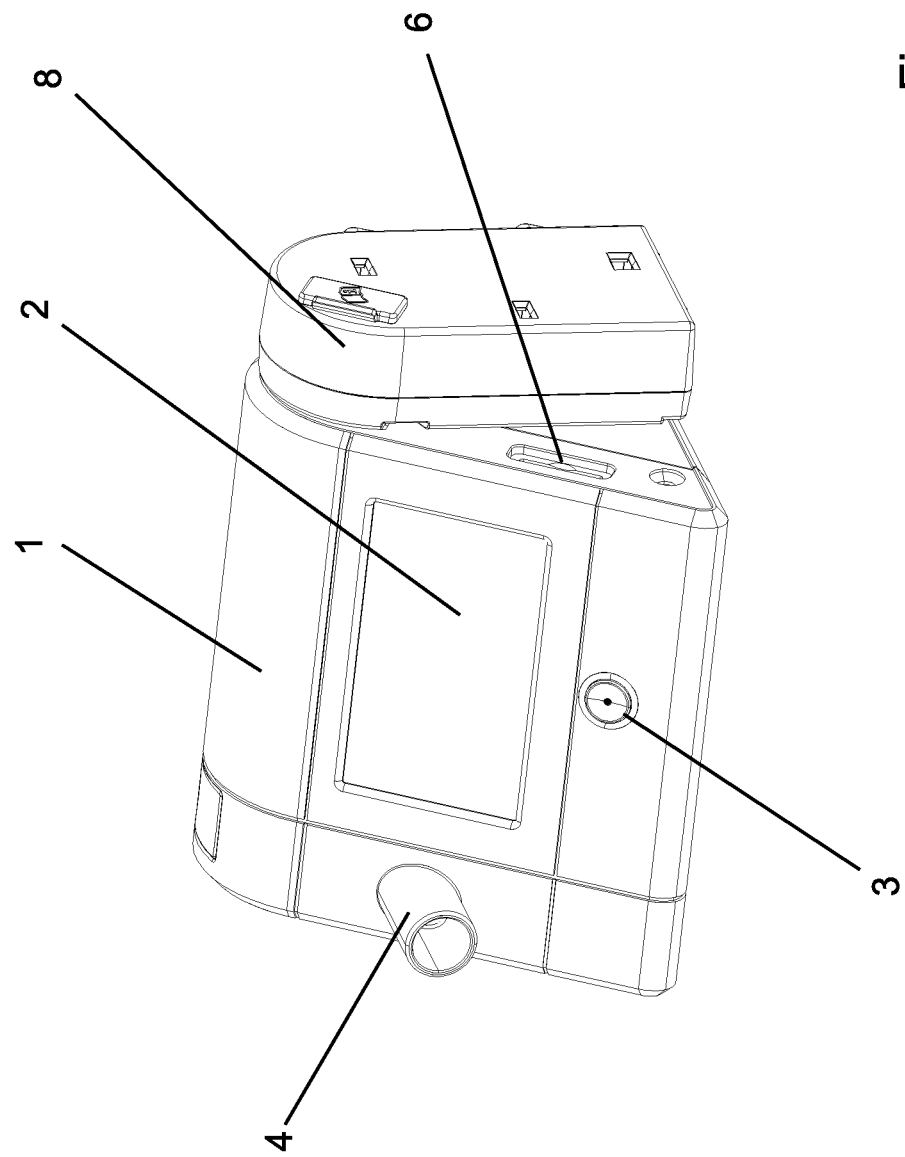
FIG. 2 shows a perspective representation of a modified device configuration.

According to the embodiment represented in FIG. 2, in the case of the arrangement of the device according to FIG. 1 the respiratory gas humidifier (7) has been removed from the respirator (1).

It is evident from looking at FIG. 1 together with FIG. 2 that, irrespective of the use of a respiratory gas humidifier (7), the same tube connection (4) can always be used. It is consequently not necessary to change over the respiratory tube according to the device function.

Figure 3:
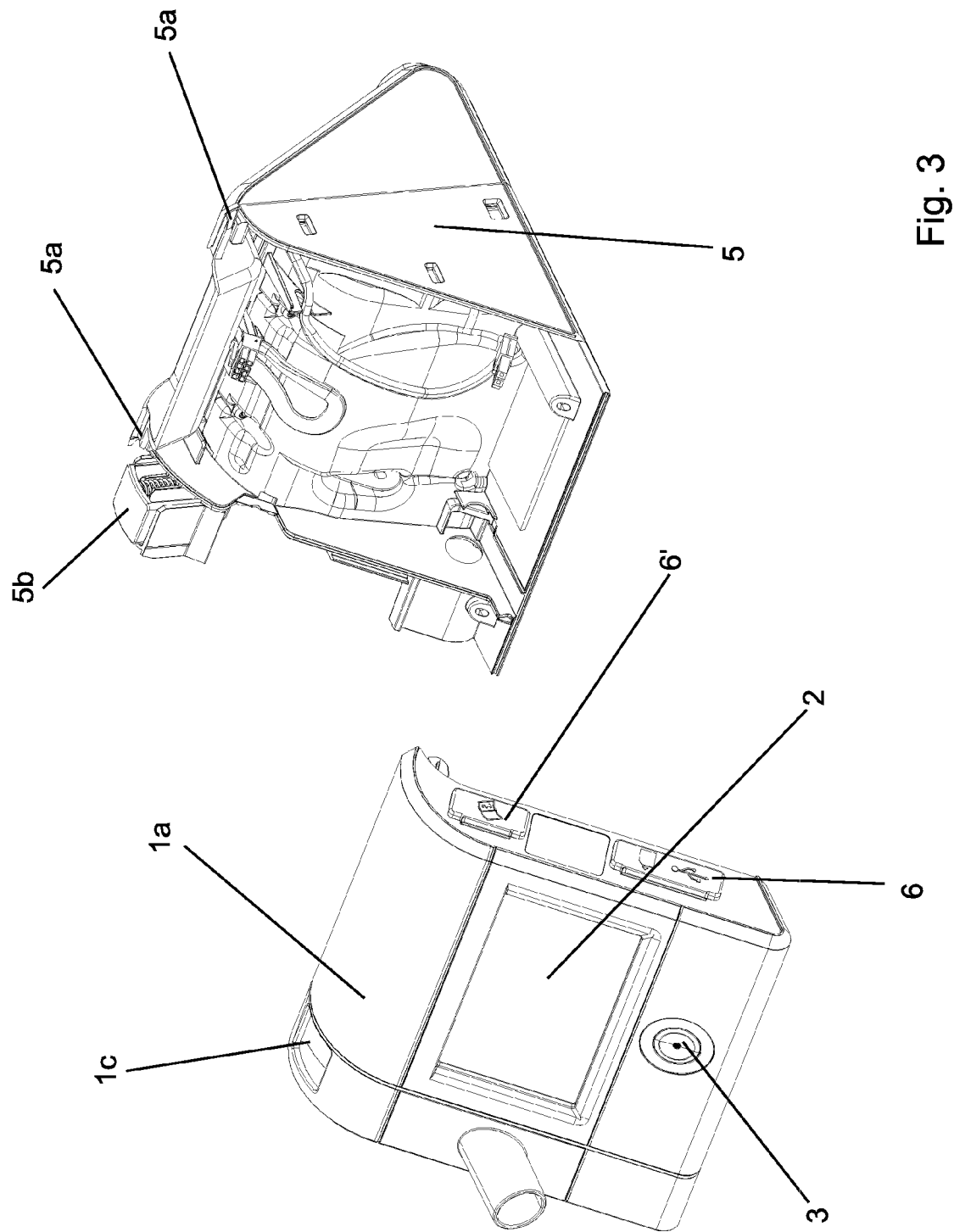
FIG. 3 shows a perspective representation of a front unit and an assembled blower box.

FIG. 3 illustrates that, with regard to its basic mechanical structure, the respirator (1) consists of two components. They are a front unit (1a), with the operating element (3) and the indicating device (2), and the blower box (5), with a front part (16), a supporting part (11) with the blower (9) and a rear part (17). The front part (16) and the rear part (17) enclose an interior device space (18) in the manner of shells. Inserted into the housing parts (16) and (17) are sound-damping materials (16' and 17'), preferably of a foam material.

Figure 3A:
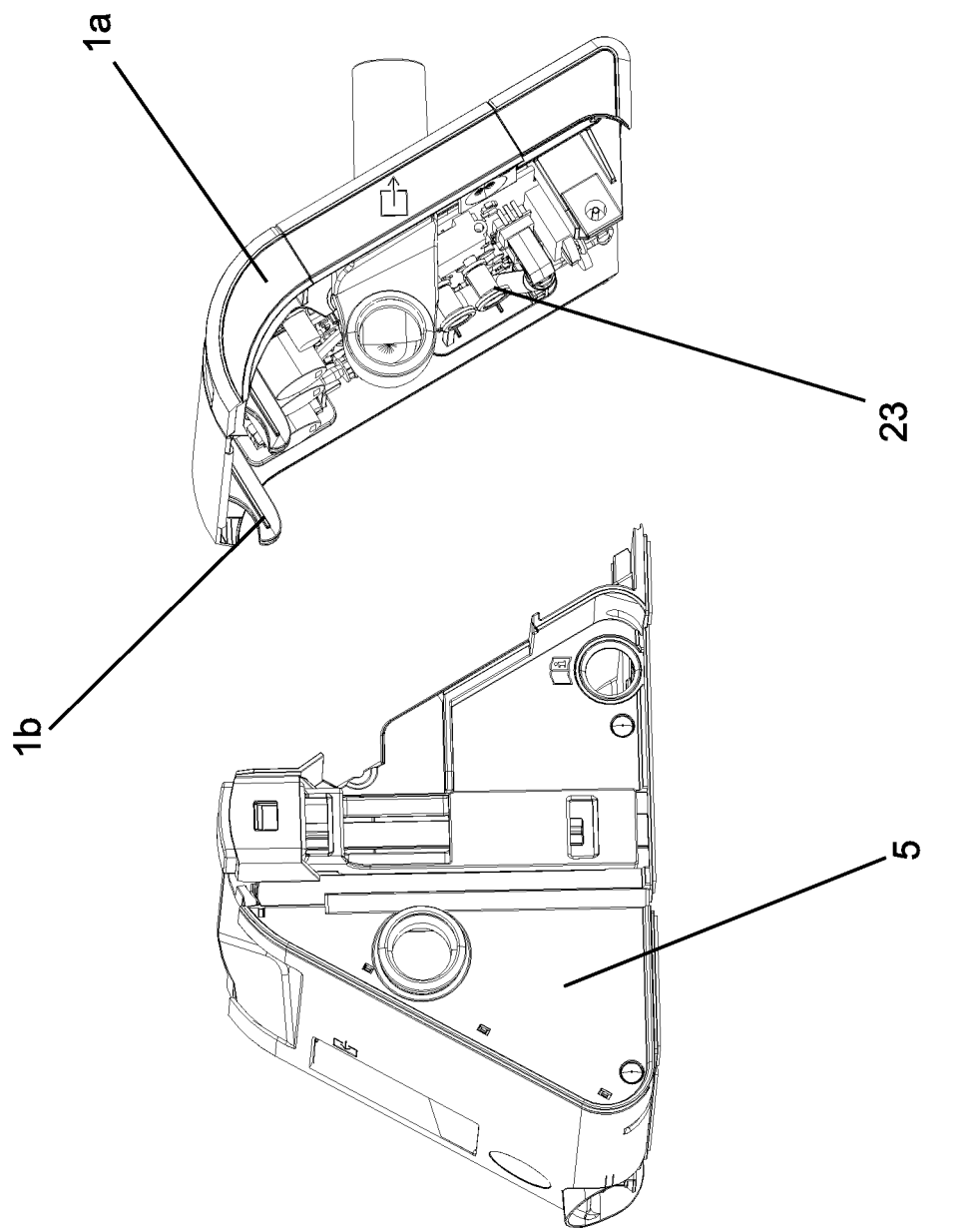
FIG. 3a shows a further perspective representation of a front unit and an assembled blower box.

FIGS. 3 and 3a show the respirator (1) broken down into the components that are the blower box (5) and the front unit (1a). The easy handling during the assembly of the components is evident from the figures. Apart from the housing, the front unit (1a) includes inter alia an indicating device (2), an operating element (3) and a control board (23), and also at least two interfaces. The front unit (1a) is preferably inclined in relation to the vertical and includes the indicating device (2), at least one operating element (3) and at least one control board (23), which is arranged parallel to the indicating device (2), and also at least two interfaces. The assembly of the front unit (1a) with the blower box (5) is performed by means of hooks (1b) on the front unit (1a), which engage behind regions (5a) of the blower box (5). The front unit is swung in by means of the pivot point comprising the hooks (1b) and the regions (5a). In addition, a catch (5b) arranged on the blower box (5) engages in an opening (1c) in the front unit (1a). To secure it, the front unit (1a) is connected to the blower box (5) by just 2 screws, and thereby forms the housing of the respirator (1). To release the front unit (1a) from the blower box (5), all that is necessary is to loosen the screws and disengage the catch (5b).

Figure 4:
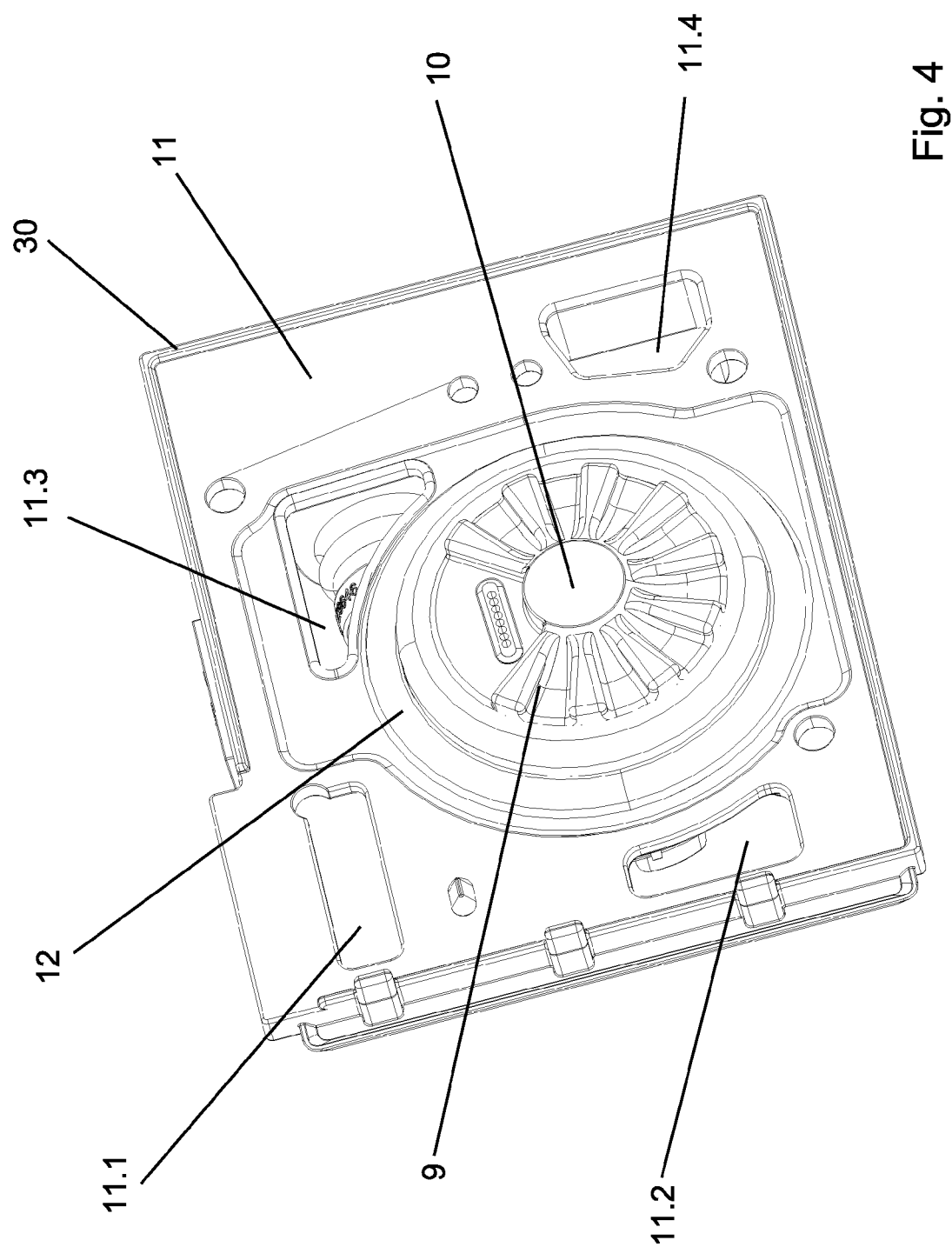
FIG. 4 shows a perspective representation of a blower arranged within the blower box, the blower being secured by a peripheral membrane structure.

According to the embodiment in FIG. 4, a blower (9) is arranged within the blower box (5). The blower (9) is typically driven by an electric motor (10).

To assist easy assembly and disassembly, the blower (9) may be secured by a—preferably elastic or viscoelastic—supporting part (11), which can be inserted into the blower box (5).

To assist structure-borne sound decoupling, the blower (9) is connected to the supporting part (11) by a likewise (visco)elastic coupling element (12). The supporting part (11) and the coupling element (12) are preferably formed as one part. They may for example be made of an elastomeric material. Elastomeric materials have the advantage that they have both elastic and viscous properties, and consequently absorb vibrational energy or convert it into heat. According to a preferred embodiment, the coupling element (12) surrounds the blower (9) in the manner of a frame. Depending on the respective application requirements, the coupling element (12) may be designed in the manner of a ring. The coupling element (12) preferably has a bead or a similar design element—for example similar to elastic suspension elements that are used in the case of loudspeakers—in order to be able to absorb vibrations better over a longer decoupling path. The blower (9) is elastically suspended in the space inside the device by the (visco)elastic coupling element (12) and/or the supporting part (11). As a result, structure-borne sound transmission to the housing (1, 16, 17) is effectively avoided. In addition, elastic spacing elements (27), which are preferably formed as one part with the coupling element (12) and/or the supporting part (11), may be provided, effectively avoiding contact of the blower with the housing (1, 16, 17). For this purpose, the spacing elements may be provided on one side or both sides of the coupling element (12) and/or the supporting part (11) and extend for example in the vertical direction.

The supporting part (11) with the coupling element (12) preferably consists of a viscoelastic material, for example of silicone.

Apart from the coupling element (12), the supporting part (11) includes various air openings (11.1, 11.2, 11.3, 11.4), in order to achieve a longer air path, and consequently a further reduction of the noise. Further redirections of the flow can also be achieved by means of the coupling element.

Figure 5:
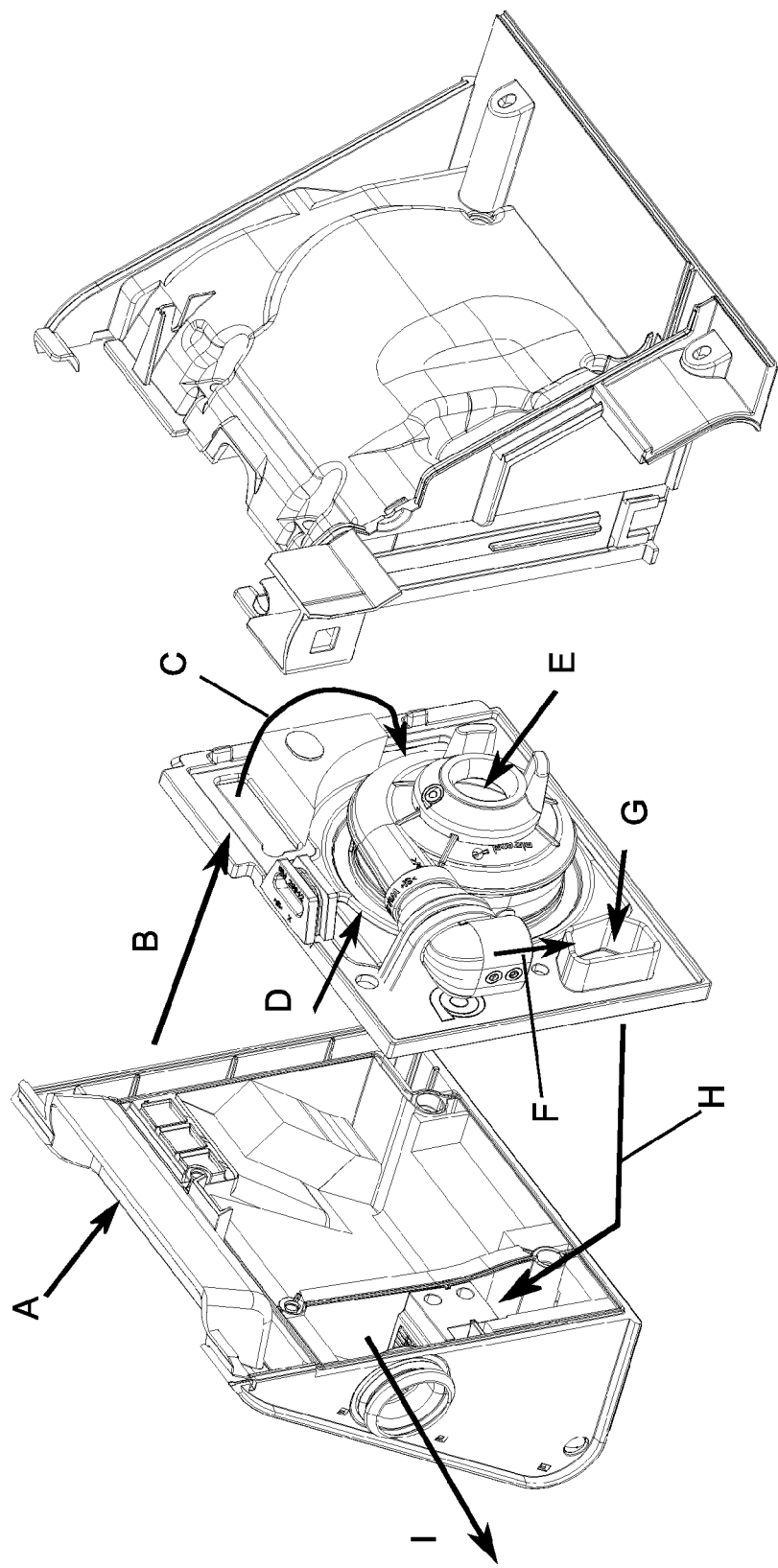
FIG. 5 shows a perspective representation of a partly disassembled blower box with depicted air conduction.

Apart from receiving the blower (9) and the specifically intended gas flow through the interior device space (18) of the blower box (5), which is illustrated in FIG. 5, the supporting part (11) also serves for providing the seal between the housing parts (16) and (17). The outer contour of the supporting part (11) receives the contour of the housing parts (16 and 17) and thus provides a seal between the housing parts (16 and 17) in the peripheral region. The supporting part (11) is preferably clamped or fitted vertically between the housing parts (16 and 17) and held by fixing the housing parts (16 and 17) against one another (for example by screwing). The viscoelastic properties of the supporting part (11) thus have the effect that the housing parts (16 and 17) are sealed. For this purpose, the supporting part has a seal (30), which for example runs around the periphery or is interrupted, and is for example formed as an edge. The housing parts (16 and 17) have sealing surfaces (31, 32) that complement the sealing edge (30).

The supporting part (11) serves for directing the air flows and for this purpose has openings or apertures (11.1, 11.2, 11.3, 11.4). The supporting part (11) likewise serves for sound damping and for this purpose has a collar (28) at least on one of the openings (11.4). The supporting part (11) likewise serves for sound decoupling and securing the blower and is therefore produced from an elastomeric material and for this purpose has a coupling element (12) for securing the blower. The coupling element (12) may also have beads, to avoid the transmission of structure-borne sound. The supporting part (11) also has at least one seal (30) for providing a seal of the housing parts (16 and 17) with respect to the surroundings by means of the sealing surfaces (31, 32) and a further seal (33) for providing a seal of the intake region and the high-pressure region by means of the sealing surfaces (34, 35). The supporting part is also formed as one part and is held between the housing parts (16 and 17) by clamping or bracing or screwing.

Figure 4A:
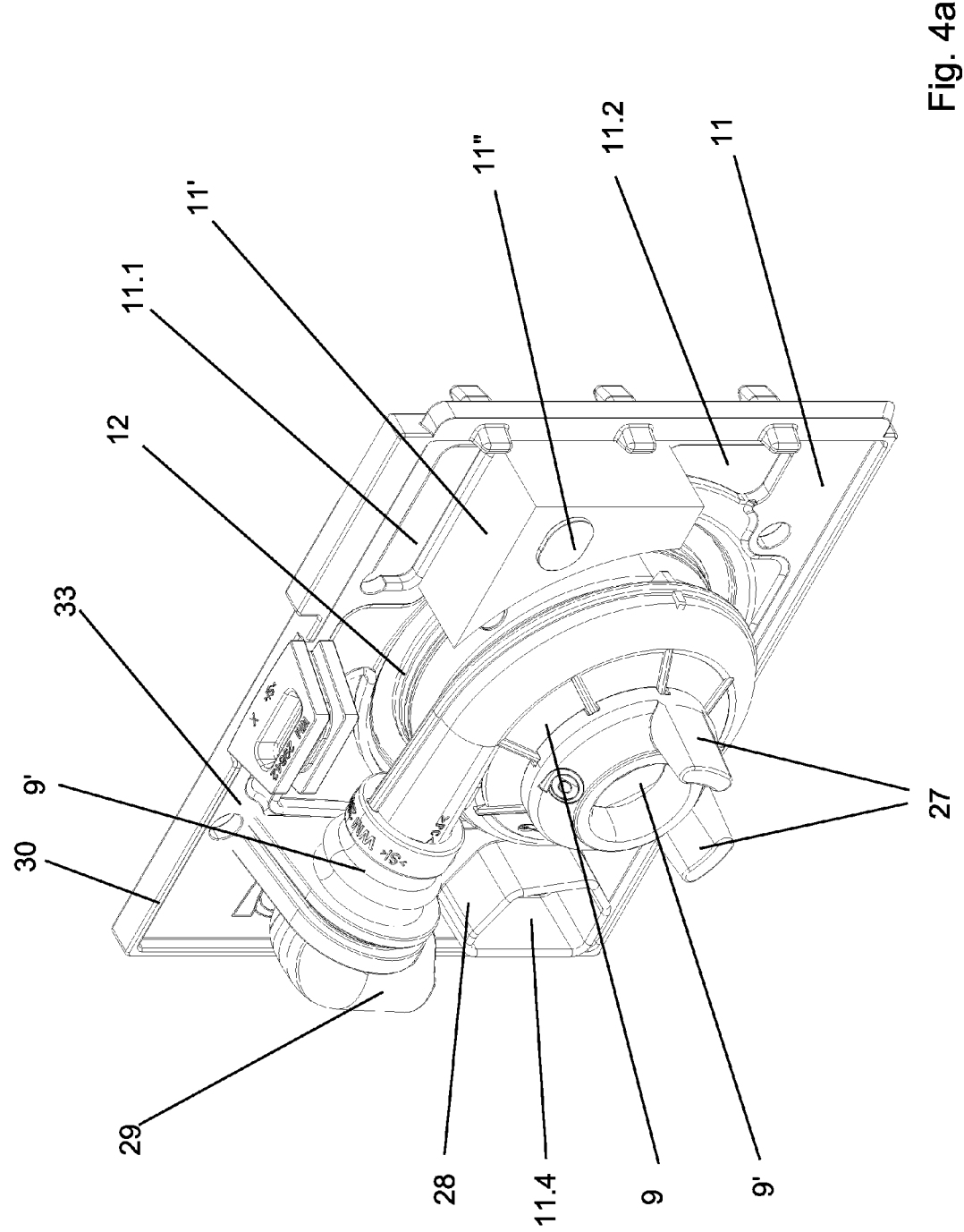
FIG. 4a shows a further perspective representation of the blower secured by a peripheral membrane.

FIG. 4a shows the supporting part (11) in a further view. Here, the intake region (9') and the air outlet (9") of the blower (9) can be seen. An additional foam-material element (11'), which is held on the supporting part (11) by means of a lug (11"), serves for redirecting the air, and consequently for reducing noise.

FIG. 5 illustrates a typical air flow through the blower box (5). According to A, air is sucked in through an intake opening in the rear part (16) and, according to B, flows through the opening (11.1) in the supporting part (11). According to C, the air flow is redirected vertically through a chamber (17.1) in the front part (17) and passes through the opening (11.2) in the supporting part (11) back into the rear part (16), into the air chamber in the region (16.2). There, the air is redirected diagonally and, according to D, flows through the opening (11.3) and, diagonally redirected further according to E, in the region (9') flows into the blower (9). The air transported by the blower (9) leaves the blower through the air outlet (9") according to F in the region (17.2) in the front part (17) and further according to G through the opening (11.4) in the supporting part (11). According to H, the air flow reaches the rear part (16) in the region (16.1), flows there through a flow measuring device and is redirected again according to I, and leaves the rear part (16) to a sound damper or to the respiratory gas humidifier.

Figure 6:
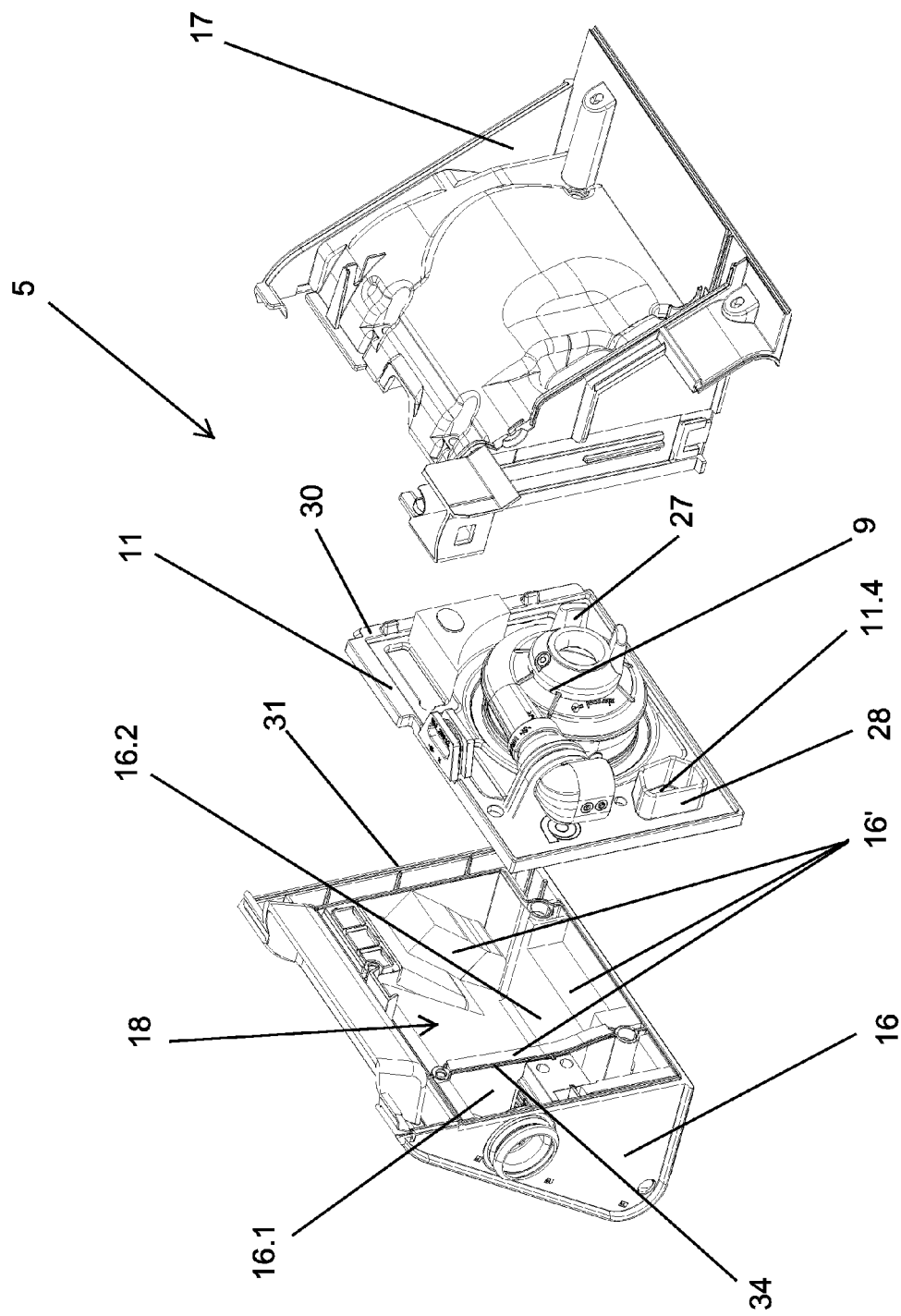
FIG. 6 shows a representation corresponding to FIG. 5 without depicted air conduction.

FIG. 6 shows the components according to FIG. 5 for a more detailed explanation of the mechanical construction without the flow arrows of the gas flow being depicted. The supporting part (11) preferably has at least one opening or an aperture (11.1, 11.2 . . . ), which serves for directing the air. The supporting part (11) preferably has at least one opening or an aperture (11.4), which is surrounded at least in certain portions by an elevated collar (28). The collar may be present on one or both sides of the aperture (11.4). The collar (28) is connected on one side to the supporting part (11) and serves for directing the air and damping airborne sound. The air transported by the blower (9) leaves the blower through the air outlet (9"). Just behind the air outlet, the accelerated air is redirected by approximately 90° by a flow redirecting feature (29), and is thus conducted in the direction of the aperture (11.4) with the collar (28).

Figure 7:
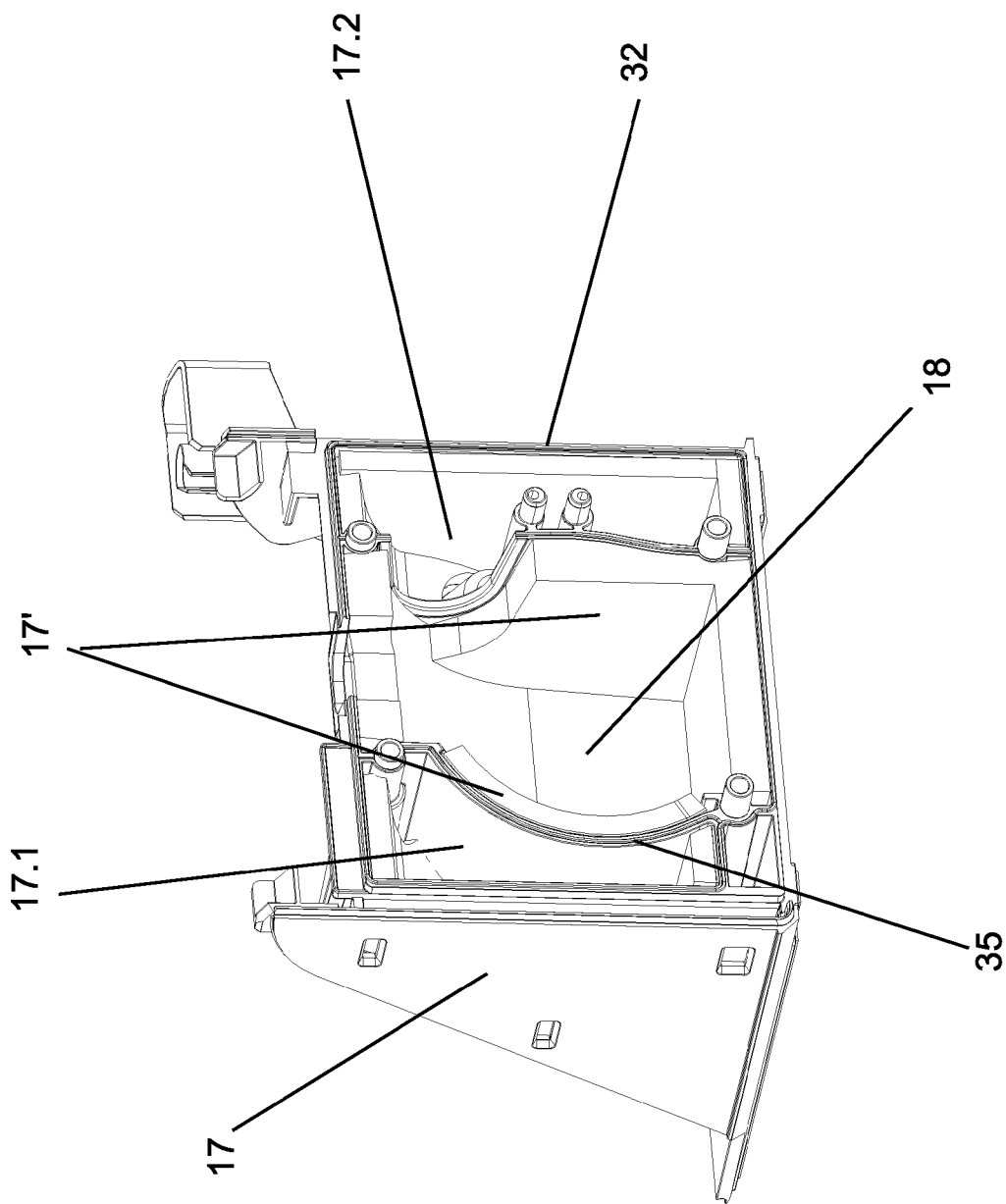
FIG. 7 shows a perspective inside view of a housing part.

FIG. 7 shows the interior housing space (18) in the front part (17), with inserted sound-damping materials (17') and the air chambers (17.1) and (17.2). According to the invention, the air chambers (17.1) and (17.2) are the high-pressure region (17.1) and the low-pressure region or intake region (17.2). Correspondingly, the two housing parts (16, 17) respectively have the associated chamber halves of the high-pressure region (16.1 17.1) and the intake region (16.2, 17.2).

For separating the high-pressure region (16.1, 17.1) and the intake region (16.2, 17.2) the supporting part (11) has a seal (33), which is clamped vertically between the housing parts (16 and 17) and is held by fixing the housing parts (16 and 17) against one another (for example by screwing). The housing parts (16 and 17) have sealing surfaces (34, 35) that complement the seal (33).

Thus, the way in which the supporting part and the housing parts (16, 17) interact produces different spaces that are sealed with respect to one another. The supporting part (11) seals off the high-pressure region (16.1, 17.1) from the intake region (16.2, 17.2). The supporting part (11) also seals off the two housing parts (16, 17). This creates four chambers, which communicate with one another and direct the air through the openings (11.1, 11.2, 11.3, 11.4).

Figure 8:
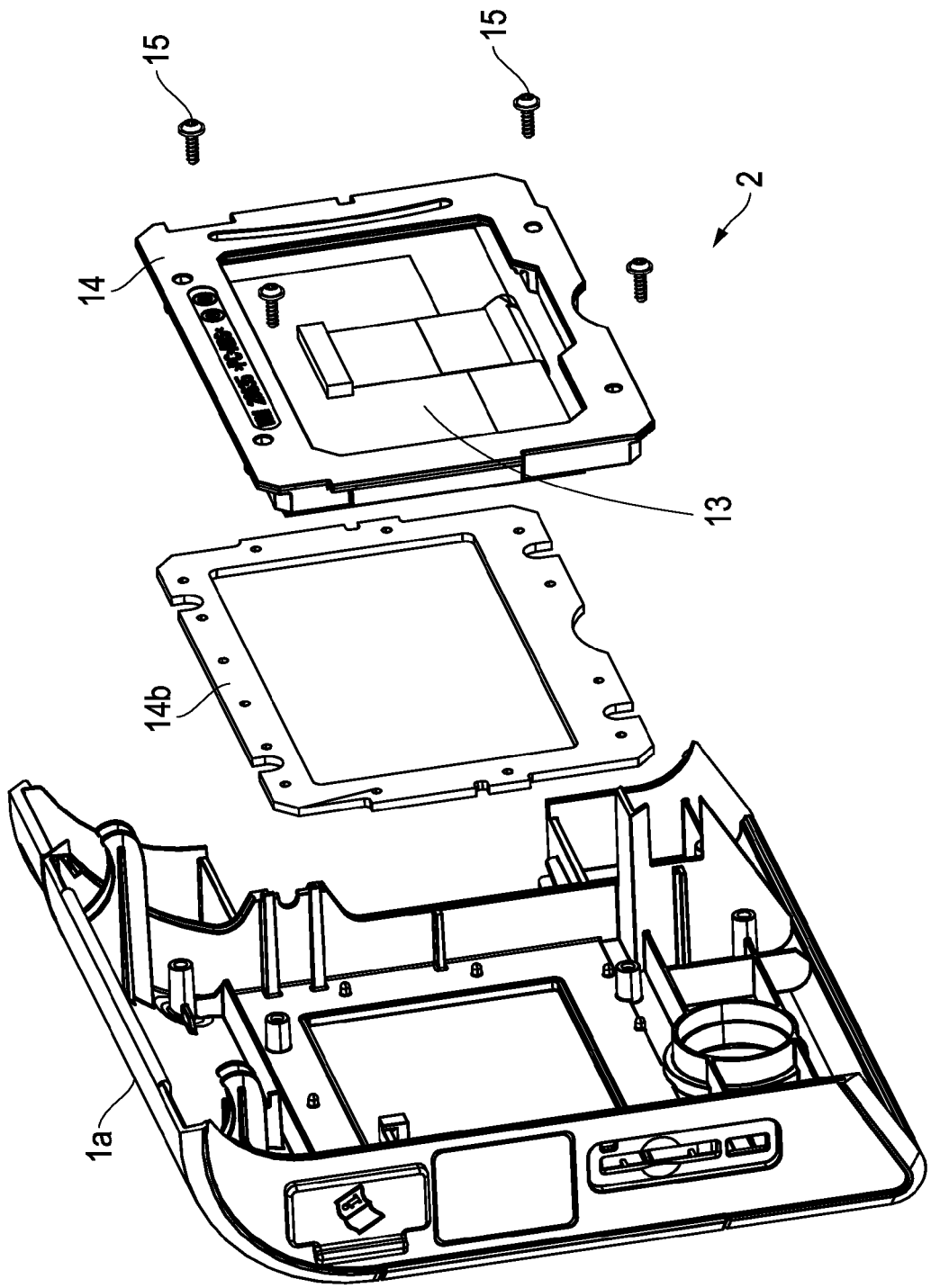
FIG. 8 shows a perspective representation to illustrate securement of an indicating device formed as a display within the housing by using a frame.
Figure 9:
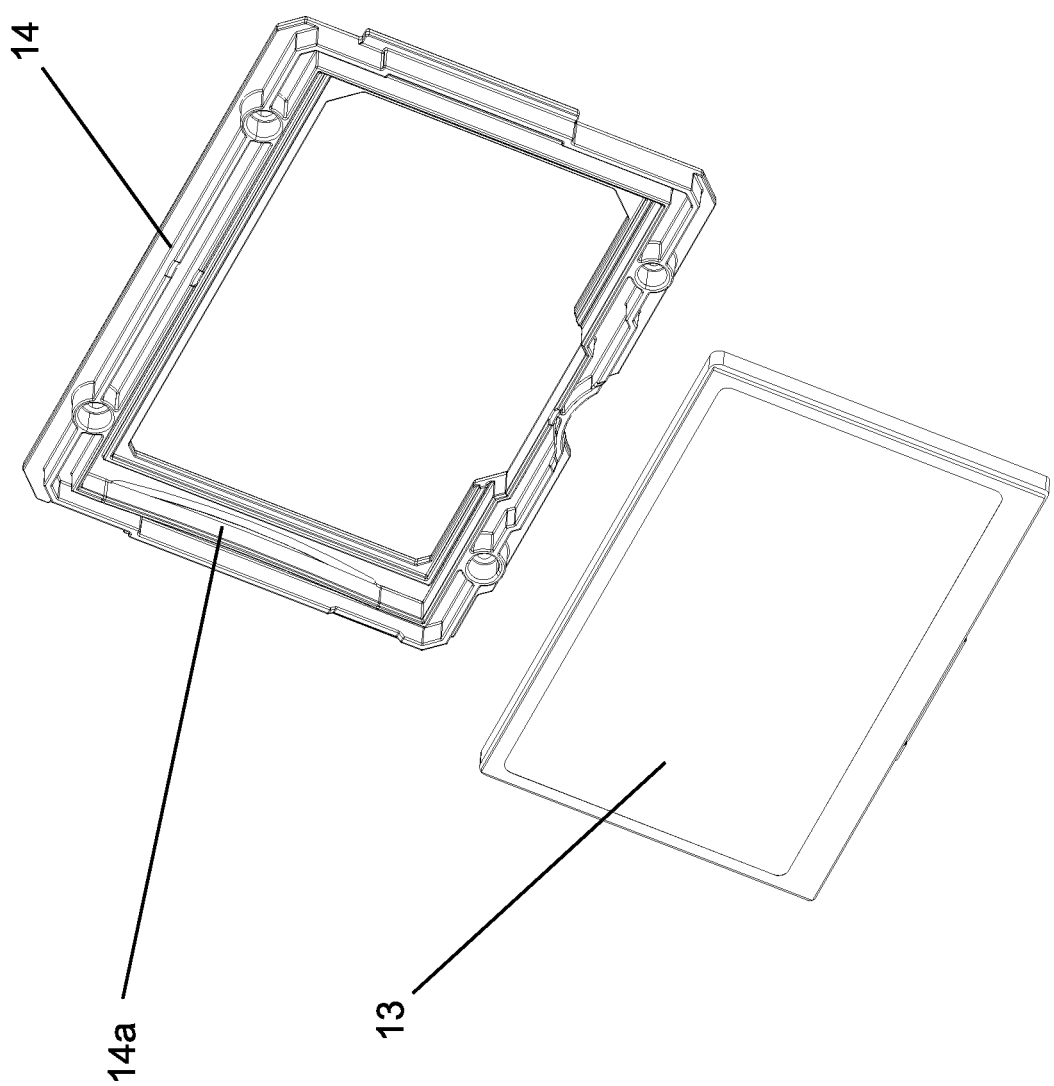
FIG. 9 shows a further representation of the display and the holding frame.
Figure 10:
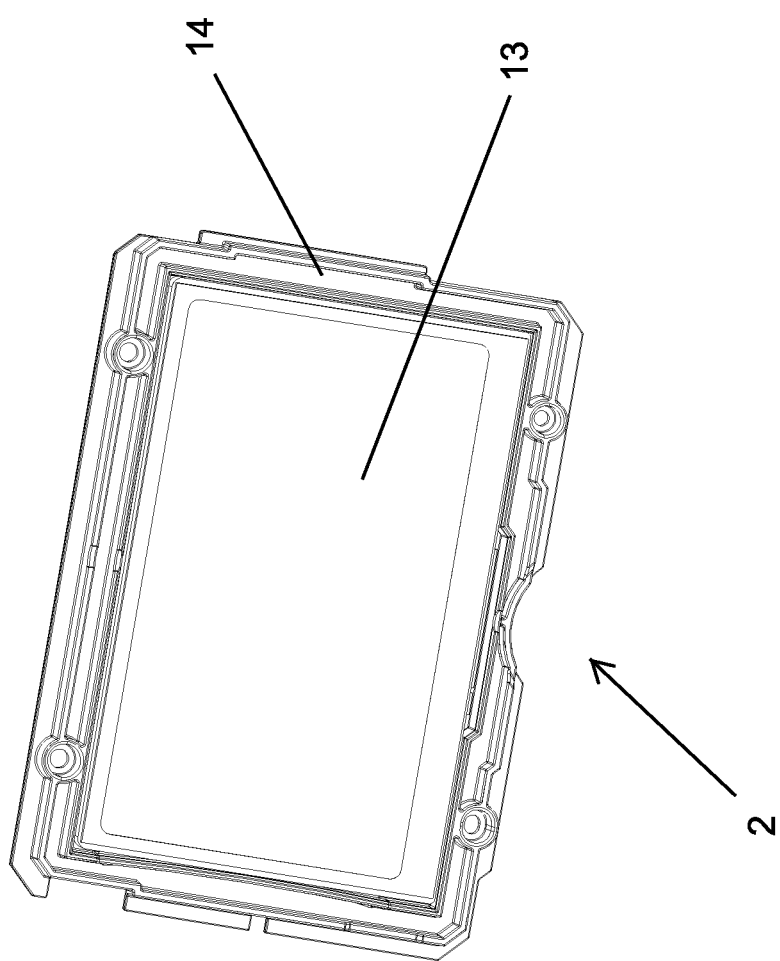
FIG. 10 shows a combined representation of the display and the holding frame.

According to the embodiment in FIG. 8, the indicating device (2) is formed as a display (13). The display (13) is designed in the manner of a panel and is fixed within the housing (5) by means of a frame-like securing element (14). It is preferably envisaged to insert the display (13) into the securing element (14) and fix it in the securing element (14) by means of a clasp (14a). This serves for better fixing of the display in the housing, since the display is fitted into the housing while inverted, and without a clasp may slip. The securing element (14) is also designed in such a way that it can compensate for production tolerances of the display (13) by varying tensioning of the clasp (14a). The individual parts are represented in FIG. 9 and the preassembled unit comprising the display (13) and the securing element (14) is represented in FIG. 10. The preassembled unit is braced against the housing (5) by using screws (15). A seal (14b) is preferably arranged between the display (13) and the housing (1a). If a different display (13) is used, for example from a different manufacturer, in this embodiment only the securing element (14) need be adapted to the display; the housing structure can be retained.

For example, the display may also be inserted into the front unit from the outside, the frame then being an integral part of this front part. In this embodiment, the front part is formed with the additional use of a front sheet or operating sheet, which is likewise placed onto the front element from the front, whereby the display is received and held between the housing part and the front sheet. In a once again preferred embodiment, the operating sheet substantially covers the externally visible part of the front part. As an alternative or in addition to the touch-sensitive areas on the display that are described further above, further operating functions may be integrated in the front sheet.

Figure 11:
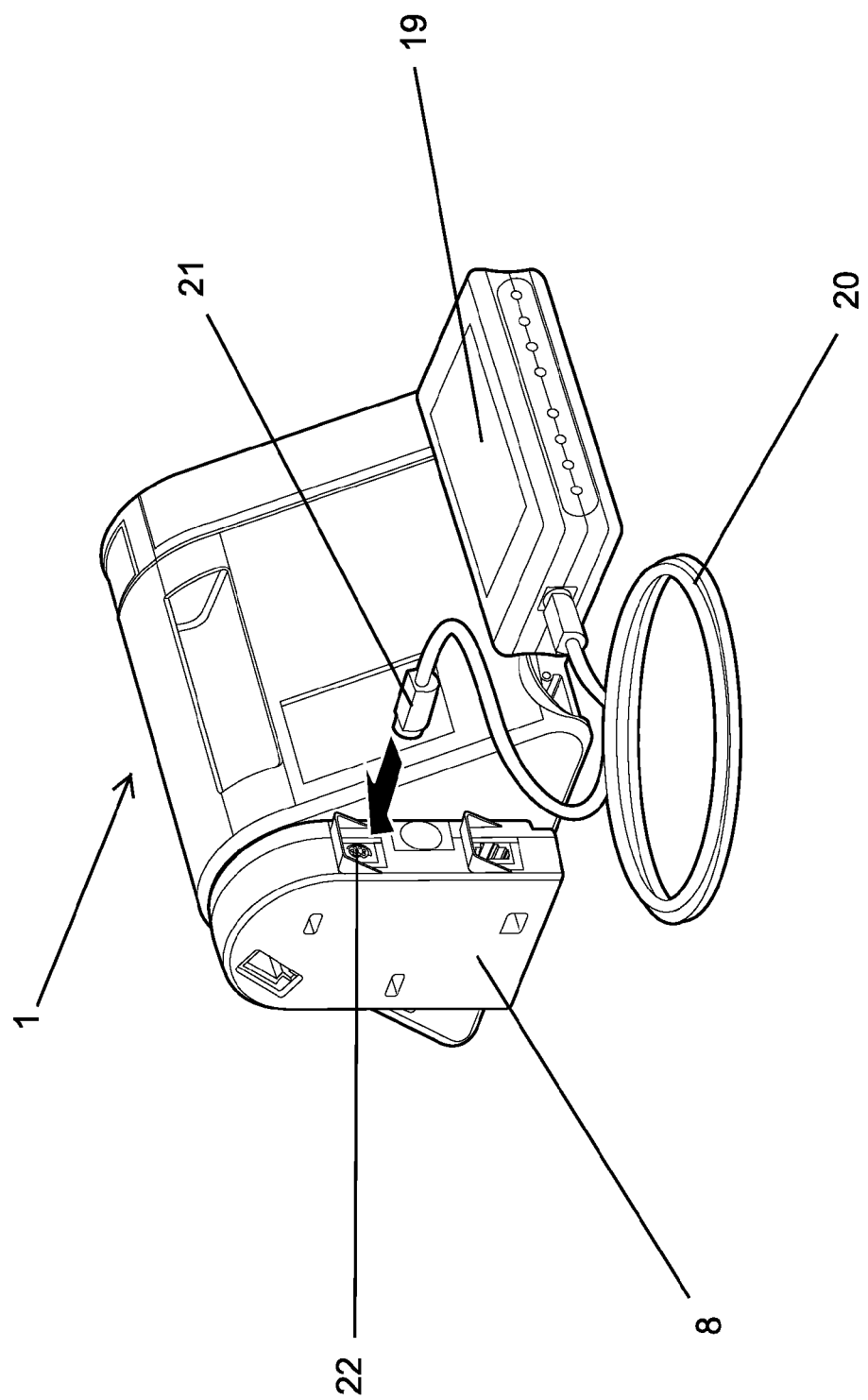
FIG. 11 shows a further perspective representation of the respirator with an assigned external operating unit and FIG. 12 shows a plan view of a control board with a pressure measuring tube, arranged within the device housing.

FIG. 11 shows an embodiment in which the respirator (1) is provided with an additional element (8) formed as a communication module. The additional element (8) serves here for the connection to a polysomnography device (PSD) (19). Coupling of the PSD (19) may take place by using a cable (20), which can be coupled to an interface (22) of the additional element (8) by means of a connector (21).

Figure 12:
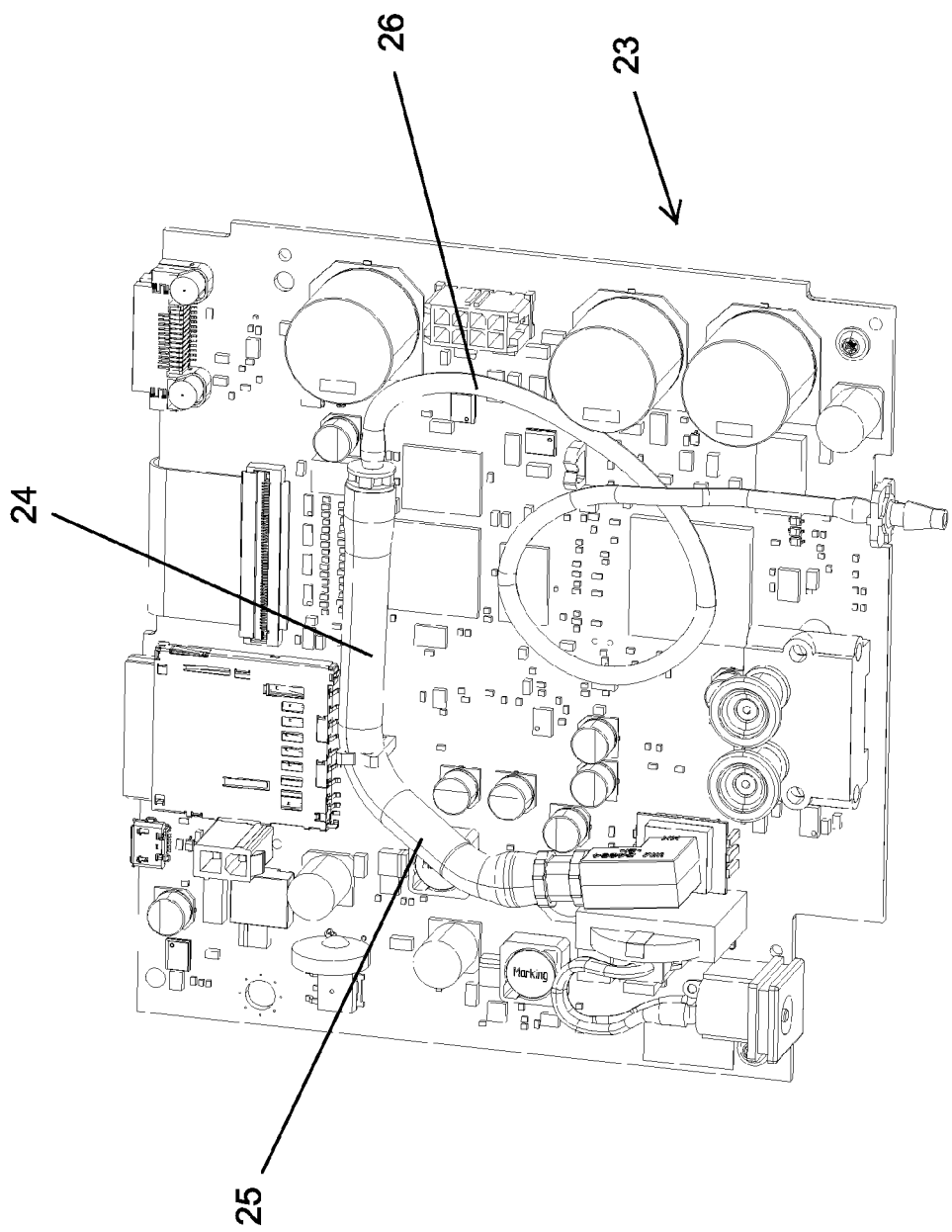

FIG. 12 shows a plan view of a control board (23), which can be arranged within the front unit (1a) of the respirator (1). The control board (23) assists a pressure measurement and is provided with a connectable tube (24) for passing on the pressure.

According to the exemplary embodiment represented, the tube (24) consists of a first tube portion (25) of a first diameter and a second tube portion (26) of a second diameter. The first diameter is greater than the second diameter.

The combination of the first tube portion (25) and the second tube portion (26) provides signal filtering, which in particular filters out harmonics present in the pressure signal. As an alternative to the filter taking a mechanical form provided by the tube portions (25, 26), electrical, electronic or software-based filtering is also possible in principle.

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

To sum up, the present invention provides:

1. A device for artificial respiration, which has a blower connected to a control, wherein both the control and the blower are arranged in a housing, and wherein the control is connected to at least one indicating device and also at least one operating element, the blower (9) being secured in the housing by a viscoelastic or elastomeric supporting part (11).
2. The device according to item 1, wherein the housing (1) consists of or comprises a front unit (1a), which has the indicating device (2), and two further housing parts (16, 17), which form a blower box (5).
3. The device according to items 1 or 2, wherein the supporting part (11) is secured between the housing parts (16, 17), the two housing parts (16, 17) respectively comprising the associated chamber halves of the high-pressure region (16.1, 17.1) and the intake region (16.2, 17.2).
4. The device according to one or more of items 1 to 3, wherein the supporting part (11) is arranged in the vertical direction between the housing parts (16, 17).
5. The device according to at least one of the preceding items, wherein the supporting part (11) forms a first seal (30), which provides a seal with respect to sealing surfaces (31, 32) of the housing parts (16 and 17), and forms a second seal (33), which provides a seal with respect to the sealing surfaces (34, 35) of the two housing parts (16, 17) and thus pneumatically separates the high-pressure region (16.1, 17.1) from the intake region (16.2, 17.2).
6. The device according to at least one of the preceding items, wherein the supporting part (11) in the blower box (5) serves for redirecting the air, and consequently reducing the noise, and for this purpose has at least two openings (11.1, 11.2, 11.3, 11.4).
7. The device according to at least one of the preceding items, wherein the supporting part (11) has at least one opening (11.4) that is surrounded at least in certain portions by a collar (28).
8. The device according to at least one of the preceding items, wherein at least three redirecting features (A, B, C, D, E, F, G, H, I) are arranged within the blower box (5) for a flow of respiratory gas.
9. The device according to at least one of the preceding items, wherein at least one sound-damping element (11', 11", 12, 17', 28) is arranged within the blower box (5) and/or on the supporting part (11).
10. The device according to at least one of the preceding items, wherein the indicating device (2) and also a front sheet that has at least one operating element are accommodated in the front unit (1a).
11. The device according to at least one of the preceding items, wherein an indicating device (2) is arranged in an inclined manner in relation to the vertical direction.

12. The device according to at least one of the preceding items, wherein the housing has a triangular cross-sectional area.

13. The device according to at least one of the preceding items, wherein the front unit comprises or consists of a vertically extending first segment and a second segment, which is inclined in relation to the vertical direction and in which an indicating device (2) is arranged.

14. The device according to at least one of the preceding items, wherein the indicating device (2) is formed as a panel-like display (13), which is fixed in the front unit (1a) by a frame-like securing element (14).

15. The device according to at least one of the preceding items, wherein the securing element (14) provides a clasp (14a) for fixing the display (13) or wherein the securing element (14) can be screwed in the front unit (1a).

16. The device according to at least one of the preceding items, wherein only one mechanical operating element (3) is provided for the activation of a device function.

17. The device according to at least one of the preceding items, wherein, in addition to the only one mechanical operating element (3), further operating areas are provided on the display (13) formed as a touchscreen.

18. The device according to at least one of the preceding items, wherein a line routing (24) for the connection of a pressure measurement comprising a line portion of a first diameter (25) and a line portion of a second diameter (26) is formed within the device (1), the second diameter (26) being smaller than the first diameter (25).

What is claimed is:

1. A device for artificial respiration, wherein the device comprises a blower connected to a control, both the control and the blower being arranged in a housing, and the control being connected to at least one indicating device and at least one operating element, wherein the blower is secured in the housing by a supporting part of a viscoelastic or elastomeric material on which the blower is arranged, and wherein at least one of (i) the supporting part comprises at least two air openings, (ii) the supporting part forms a first seal, which provides a seal with respect to sealing surfaces of two housing parts, and forms a second seal, which provides a seal with respect to different sealing surfaces of the two housing parts and thus pneumatically separates a high-pressure region from an intake region, and (iii) elastic spacing elements which prevent contact between the blower and the housing are provided on one side or both sides of the supporting part.

2. The device of claim 1, wherein the housing comprises or consists of a front unit, which comprises the indicating device, and two further housing parts, which form a blower box.

3. The device of claim 2, wherein at least three redirecting features for a flow of respiratory gas are arranged within the blower box.

4. The device of claim 2, wherein at least one sound-damping element is arranged within the blower box and/or on the supporting part.

5. The device of claim 1, wherein the viscoelastic or elastomeric material comprises a silicone.

6. The device of claim 1, wherein the supporting part comprises at least two air openings.

7. The device of claim 1, wherein the supporting part is secured between two housing parts, the two housing parts respectively comprising associated chamber halves of a high-pressure region and an intake region.

8. The device of claim 1, wherein the supporting part is arranged in a vertical direction between housing parts.

9. The device of claim 1, wherein the supporting part forms a first seal, which provides a seal with respect to sealing surfaces of two housing parts, and forms a second seal, which provides a seal with respect to different sealing surfaces of the two housing parts and thus pneumatically separates a high-pressure region from an intake region.

10. The device of claim 1, wherein the supporting part comprises at least one opening that is surrounded at least in portions thereof by a collar.

11. The device of claim 1, wherein a line routing for connecting a pressure measurement comprising a line portion of a first diameter and a line portion of a second diameter is present within the device, the second diameter being smaller than the first diameter.

12. The device of claim 1, wherein elastic spacing elements which prevent contact between the blower and the housing are provided on one side or both sides of the supporting part.

13. A device for artificial respiration, wherein the device comprises a blower connected to a control, both the control and the blower being arranged in a housing, and the control being connected to at least one indicating device and at least one operating element, wherein the blower is secured in the housing by a supporting part of a viscoelastic or elastomeric material on which the blower is arranged, the blower being connected to the supporting part by a coupling element, and wherein at least one of (a) the coupling element surrounds the blower in the form of a frame, (b) the coupling element comprises beads to prevent transmission of structure-borne sound, and (c) elastic spacing elements which prevent contact between the blower and the housing are provided on one side or both sides of the coupling element and/or the supporting part.

14. The device of claim 13, wherein the supporting part and the coupling element are formed as one part.

15. The device of claim 13, wherein the coupling element surrounds the blower in the form of a frame.

16. The device of claim 15, wherein the coupling element is present as a ring.

17. The device of claim 13, wherein the blower is elastically suspended inside the housing by the supporting part and/or the connecting element.

18. The device of claim 13, wherein elastic spacing elements which prevent contact between the blower and the housing are provided on one side or both sides of the coupling element and/or the supporting part.

19. The device of claim 13, wherein the coupling element comprises beads to prevent transmission of structure-borne sound.

20. The device of claim 13, wherein the supporting part is arranged in a vertical direction between housing parts.

* * * * *